United States Patent [19]

Shofner et al.

[11] Patent Number: 5,138,879
[45] Date of Patent: Aug. 18, 1992

[54] METHOD FOR PRODUCING MULTIPLE FIBER DATA

[75] Inventors: Frederick M. Shofner; Youe-T Chu; Christopher K. Shofner; Mark G. Townes, all of Knoxville, Tenn.

[73] Assignee: Zellweger Uster, Inc., Knoxville, Tenn.

[21] Appl. No.: 724,385

[22] Filed: Aug. 23, 1991

Related U.S. Application Data

[60] Division of Ser. No. 460,292, Jan. 3, 1990, abandoned, which is a continuation-in-part of Ser. No. 293,258, Jan. 4, 1989, abandoned.

[51] Int. Cl.$^5$ .................... G01L 5/06; G01L 5/10; G01N 3/08
[52] U.S. Cl. .................... 73/160; 73/828; 356/387; 356/429
[58] Field of Search .................... 73/160, 159, 828; 364/564, 562, 563; 356/384, 383, 387, 429; 250/559

[56] References Cited

U.S. PATENT DOCUMENTS

| | | | |
|---|---|---|---|
| 2,537,170 | 1/1951 | Steiding | 73/160 |
| 3,049,916 | 8/1962 | Weiner | 73/828 |
| 3,069,964 | 12/1962 | Simon | 356/385 |
| 3,079,790 | 3/1963 | MacDonnell | 73/160 |
| 3,290,932 | 12/1966 | Hitt | 73/160 |
| 3,936,665 | 2/1976 | Donoghue | 364/563 |
| 4,031,746 | 6/1977 | Furuta et al. | 73/800 |
| 4,173,787 | 11/1979 | Katona et al. | 73/160 |
| 4,511,253 | 4/1985 | Glockner et al. | 356/385 |
| 4,562,743 | 1/1986 | Bonine | 73/828 |
| 4,634,280 | 1/1987 | Paulson, Jr. | 356/385 |
| 4,764,876 | 8/1988 | Whitener, Jr. et al. | 73/160 |
| 4,891,974 | 1/1990 | Wassenhoven | 73/160 |
| 4,895,028 | 1/1990 | Mayer | 73/827 |

FOREIGN PATENT DOCUMENTS

| | | | |
|---|---|---|---|
| 0226070 | 3/1958 | Australia | 73/160 |
| 1276934 | 9/1968 | Fed. Rep. of Germany | 73/160 |
| 0011338 | 2/1981 | Japan | 73/160 |
| 0211624 | 12/1983 | Japan | 73/160 |
| 2031960 | 4/1980 | United Kingdom | 73/160 |

OTHER PUBLICATIONS

Dorrity, J. L. et al., "A Minicomputer—controlled all-digital tensile test system," Proceedings of the IEEE, vol. 63 No. 10 (Oct. 1975).
Research Disclosure, "Pick-up detector", No. 13710, p. 13 (Sep. 1975).
Skelton, J., "The Tensile Behavior of Fibrous Materials at High Rates of Strain and Subambient Temperatures," Materials Research and Standards, vol. 10, No. 6 (Jun. 1970).

*Primary Examiner*—William A. Cuchlinski, Jr.
*Assistant Examiner*—Diego F. F. Gutierrez
*Attorney, Agent, or Firm*—Luedeka, Hodges, Neely & Graham

[57] ABSTRACT

A method for producing multiple fiber data from a plurality of single fiber tests. A plurality of individual fibers are subjected to tension tests such that the individual fibers are elongated tensioned and broken while characteristics of the fiber are monitored. Multiple fiber data are obtained by testing a number of fibers from a sample and superimposing the graphical representation of tensile characteristics of the individual fibers upon one another to obtain a composite representation which constitutes multiple fiber data. Characteristics of individual fibers which may be combined to obtain a composite representation constituting multiple fiber data include such characteristics as tension, elongation and cross-sectional characteristics of the fiber.

8 Claims, 7 Drawing Sheets

METHOD FOR PRODUCING MULTIPLE FIBER DATA

This is a division of application Ser. No. 07/460,292, filed Jan. 3, 1990 now abandoned; which is a continuation-in-part application of Ser. No. 07/293,258, filed on Jan. 4, 1989, now abandoned.

FIELD OF INVENTION

The present invention relates to fiber testing and in particular to the tensile testing of fibers for obtaining data usable in fiber processing.

BACKGROUND OF THE INVENTION

For proper utilization of natural or man-made fibers it is essential to have precise, accurate, and basic tensile characteristics of the fibers. To illustrate, in the making of yarn from cotton or polyester staple, in the researching genetic influences upon characteristics of cotton or wool, or in the production of man-made fibers from carbon or glass, data relating to the tensile characteristics of the fibers commonly need to be compiled and studied. As used herein, the term "tensile" will be understood to include force-elongation characteristics and cross-sectional characteristics. For example, the traditional material characteristic of tensile stress is simply the ratio of breaking force divided by cross-sectional area; common dimensions for tensile stress are pounds/inch$^2$ or newtons/m$^2$. As a second example, percentage elongation is commonly taken as the elongation for which Hooke's Law holds (when incremental force is directly proportional to incremental elongation) divided by the untensioned length (gauge) of the material times 100%. (Note that this definition of elongation exchanges elongation components when the force is small, i.e., "crisp" or "stack", or when force is not linear with incremental elongation.)

It is desirable that such tensile data be generated quickly and in sufficient quantities to permit the statistical analysis of the fibers.

Known instruments used for obtaining tensile data on a bundle of fibers are not capable of providing data on individual fibers. In the textile industry, it is traditional to test bundles of fibers as opposed to single fibers. In part, the rationale behind this procedure is that fibers are normally used in bundles such as in cotton yarn (thread). However, these traditional test procedures do not provide much, if any, information about the single fiber. For example, a break test of a fiber bundle will not provide much information about the amount of load each fiber bears during the test or the manner in which each fiber elongates and breaks during the test. Even if the sensitivity of the force transducer is made very high, the data obtained from a fiber bundle test is masked to some extent by damaged oscillatory response of the force transducer or ringing. That is, as individual fibers in a bundle break, a ringing oscillation is inherently set up in the test device that may distort data. Since the fibers of a bundle break at varying elongations, this ringing effect is occurring throughout the majority of the test. Ringing may not significantly affect the data as to the entire bundle, but it is usually sufficient to frustrate any attempt to derive precise data as to individual fiber characteristics or contributions.

Existing instruments for testing a single fiber, such as the Instron force-elongation tester, are very slow to use due to procedures normally involved in preparing the fiber for testing. In the textile industry, individual fiber testing is seldom done because the statistical quality of data thus obtained is not viewed as useful as bundle test data.

It is therefore a general object of the present invention to provide an apparatus and method for testing single fibers wherein data accumulated are obtained quickly and in sufficient quantities to be statistically meaningful.

SUMMARY OF THE INVENTION

The present invention resides in an apparatus and method for testing of fibers, either individually or in bundles, for the compiling of data relating to characteristics of the fibers as the fibers are tensioned.

One embodiment of the apparatus for testing at least one fiber having a mid-region and two opposite ends includes a hook disposed so that the mid-region of the fiber is positionable over the hook and the fiber ends hang over opposite sides of the hook. The apparatus also includes clamp means for clamping the ends of the fiber when the fiber is positioned over the hook and translation means for moving the hook and clamp means relative to one another to tension the fiber held therebetween. Monitor means are associated with the hook and clamp means for monitoring at least one characteristic of the fiber as it is tensioned such as force-elongation, diameter, fineness, count, thickness, etc. Preferably, test zone environmental control means are provided to control the atmosphere in the immediate near vicinity of the fiber while it is being tested.

An embodiment of the method of the invention includes the steps involved in using the aforedescribed one embodiment of the apparatus. The fiber is placed so that its mid-portion is positioned across the hook and the fiber ends hang over opposite sides of the hook, and the ends of the fiber are clamped in the clamp means. The hook and clamp means are subsequently moved relative to one another to tension the fiber held therebetween, and a characteristic of the fiber is monitored as the fiber is tensioned. In the basic embodiments, force-elongation characteristics are measured.

In another embodiment of the apparatus, the apparatus includes first and second holding means for holding corresponding portions of a fiber and translation means for moving the first and second holding means relative to one another to thereby tension the fiber. The apparatus also includes electromagnetic radiation means for directing radiation onto the fiber and detector means for measuring extinction due to or the scattered radiation from the fiber. It is preferred to observe the extinction of radiation, but other angles of observation of either forward side, or back scattering may be used. The detector means produce a signal in response to the detected radiation, and processing means in the apparatus receive the detection signal and determines a cross-sectional characteristic (such as diameter or fineness or thickness) of the fiber corresponding to the detected signal.

Another aspect of the method includes the steps involved in using the aforedescribed another embodiment of the apparatus. The fiber is tensioned along its length and, at the same time, radiation is directed generally toward the fiber from one side thereof. The scattered radiation or extinction due to the fiber is detected, and a signal is produced which corresponds to the detected radiation during the time period that the fiber was under tension. A cross-sectional characteristic of the fiber is then determined in response to the produced signal.

In another aspect of the method, multiple fiber data are derived from two-coordinate graphical representations (or arrays) of elongation and force characteristics of individual fibers in the bundle. Within the graphical representations, the magnitude of fiber elongation is plotted along one coordinate, and the magnitude of force exerted upon the fiber is plotted along the other coordinate. For a preselected elongation magnitude, the force values of the graphical representations are added together to obtain an additive force value, and the additive force value is plotted on a secondary two-coordinate graph wherein one coordinate of the secondary graph denotes elongation magnitudes and the other coordinate of the secondary graph denotes a range of additive force values. Force values are added together for a number of other preselected elongation magnitudes identified on the graphical representations and the resultant additive values are plotted on the secondary graph to obtain a secondary graphical representation of force-elongation characteristics for all of the fibers tested. This secondary graphical representation constitutes multiple fiber data.

Multiple fiber data obtained by the present invention is not identical to data obtained from any known bundle test, but there is correlation between multiple fiber data and both twisted fiber bundle test and parallel (brushed) fiber tests. Generally, multiple fiber data predict an upper limit for twisted bundle tests and a lower limit for parallel bundle tests. In some instances, multiple fiber data may be more useful than bundle tests. For example, if crimp is known to significantly affect performance of fibers in a certain application, then the parallel brushed bundle test would not be appropriate because crimp is uncontrollably removed (brushed out) from the fiber before the test. On the other hand, multiple fiber data normally (but not always) include fiber crimp effects and would be more useful in predicting performance or selecting fibers for certain applications.

In the above discussion, multiple fiber data was obtained by "adding" force values from a plurality of "graphical representations". It will be understood that "graphical representations" will normally take the form of numbers in a computer, such as a numerical array, and the term graphical representation has been chosen because it best communicates visually the invention. It does not imply that the actual production of a physical graph is necessary to the invention.

Likewise, the term "added" should be understood in a broad sense. While mathematically precise adding is preferred, the graphical representations could be combined or mixed electronically in ways that might not constitute adding in a strict mathematical sense.

BRIEF DESCRIPTION OF THE DRAWINGS

The present invention may best be understood by reference to illustrative embodiments which are shown in the accompanying drawings.

DETAILED DESCRIPTION OF THE ILLUSTRATED EMBODIMENTS

Turning now to the drawings in greater detail, there is shown in FIG. 1 an embodiment 20 of a fiber tensile testing apparatus for performing a tensile test on a fiber 22. To perform a test with the apparatus 20, the fiber 22 is tensioned and characteristics such as the elongation of the fiber 22 and the magnitude of the tension forces placed upon the fiber 22 are monitored. Data collected on a plurality of single fibers as a result of the monitoring of such characteristics can be used to statistically analyze fibers like that of the fiber 22. While the embodiment 20 has been designed to rapidly test single fibers, it will be understood that fiber bundles may also be tested using this particular embodiment of the invention.

Figure 1A:
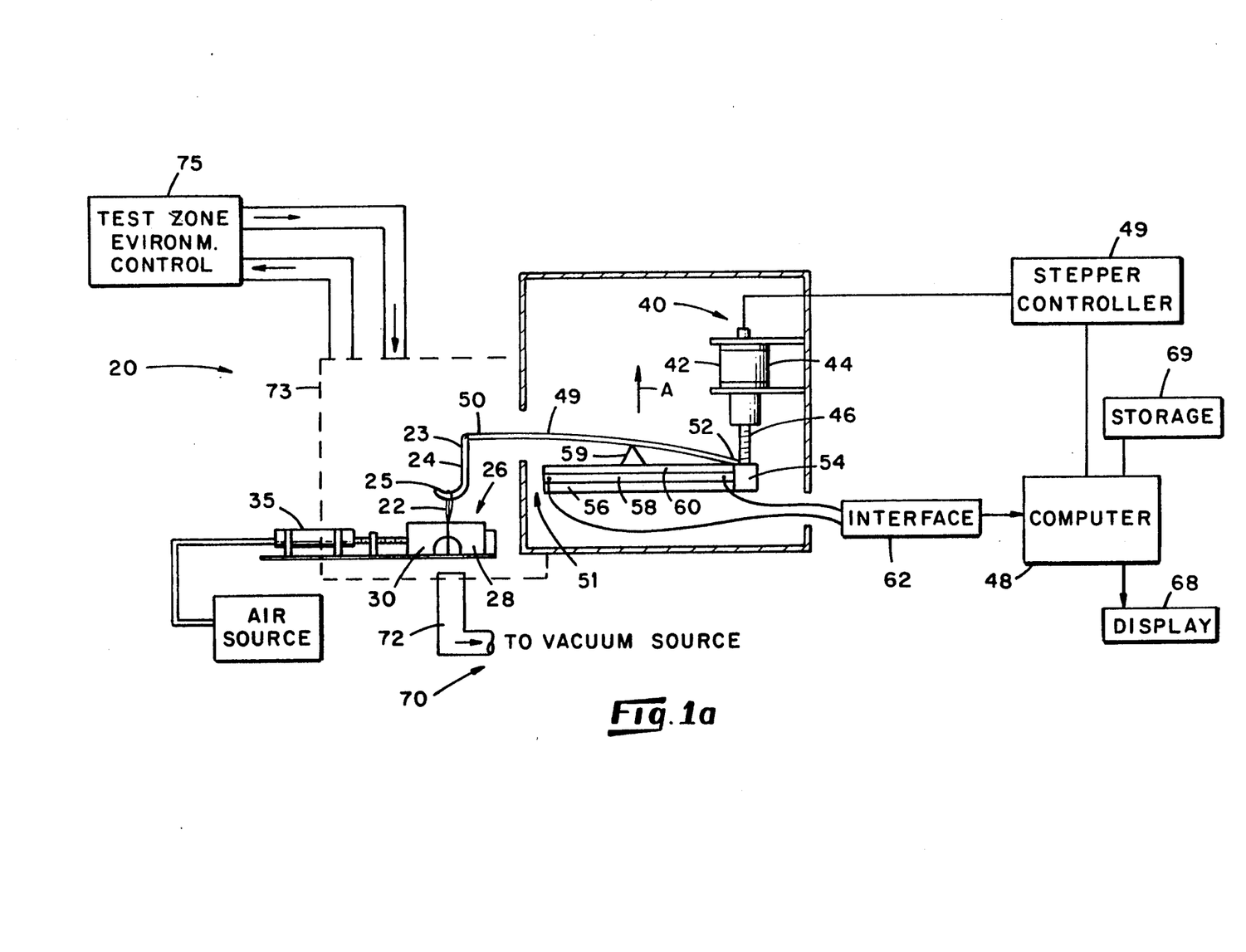
FIG. 1a is a schematic diagram of one embodiment of a fiber test apparatus.

The apparatus 20 includes a hook 24 and clamping means, generally indicated 26, disposed in such a relationship with one another that the fiber 22 can be draped across the hook 24 and partially positioned within the clamping means 26. More specifically, the hook 24 is disposed so that the mid-portion of the fiber 22 can be positioned over the hook 24 and the ends of the fiber 22 can be clamped within the clamping means 26. The gauge, the initial or untensioned distance between the hook 24 and the clamping means 26, is preferably one eighth inch (⅛") for cotton or 1 cm for polyester staple.

Figure 1B:
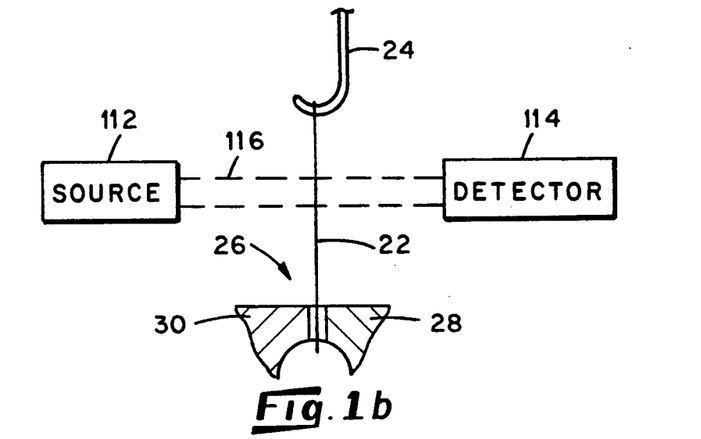
FIG. 1b is a side detail view of the hook and clamp means of FIG. 1a further showing a radiation source and detector.

The hook 24 in FIG. 1b includes a relatively rigid core 23, such as steel, and a material covering the core which provides a wear surface 25 over which the fiber 22 is draped. Preferably, the wear surface 25 is provided by a plastic material such as, for example, heat shrink tubing, to facilitate replacement of the wear surface 25 and so that frictional forces exerted upon the fiber by the hook 24 during a tensioning process are not appreciable.

Figure 2:
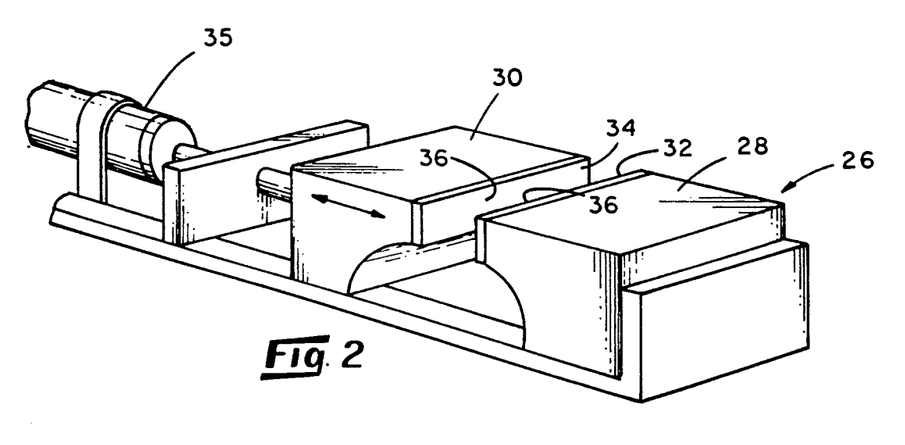
FIG. 2 is a perspective view of the clamp of the FIG. 1 apparatus drawn to a larger scale.

The clamping means 26 of the apparatus 20, best shown in FIG. 2, includes a pair of jaws 28, 30 having opposing clamping surfaces 32, 34, respectively. One jaw 28 is fixed in a stationary position and the other jaw 30 is adapted to move toward and away from the other jaw 28 in response to appropriate actuation of an air cylinder 35 so that the clamping surfaces 32, 34 move into and out of contact with one another. To prevent the fiber 22 from being cut or deformed by the clamping surfaces 32, 34 of the jaws 28, 30 each surface 32 or 34 is covered with a relatively nonresilient lining material 36, such as paper or suitable plastic. When the fiber 22 is clamped between the surfaces 32, 34 the lining material 36 prevents the fiber 22 from slipping and adds no extraneous forces to the fiber 22.

With reference again to FIG. 1, the apparatus 20 includes translational means, generally indicated 40, for moving the hook 24 and clamping means 26 relative to one another so that the fiber 22 connected therebetween is placed under tension. In the depicted embodiment 20, the translational means 40 includes a reversible stepping motor 42 having a housing 44 which is mounted in a stationary condition and a threaded shaft 46 which is mounted within the housing 44 for lengthwise movement relative thereto when the motor 42 is energized. Actuation of the motor 42 is controlled by a controller 49 which is controlled by computer 48 so that when desired, the shaft 46 is rotated and platform 51 is moved upwardly or downwardly, as viewed in FIG. 1, upon appropriate actuation of the motor 42. There is interposed between the hook 24 and the lower end of the shaft 46 an elongated connecting truss member 49 having two ends 50, 52 joining the hook 24 and platform 51. Fixed end 52 is held by an anchor member 54. A transducer 58 is mounted between a lower plate member 56 and an upper plate member 60 of the platform 51. An actuator 59 is disposed below the truss member 49 so that forces on the hook 24 are transmitted to the transducer 58 through the actuator 59. The actuator 59 is free to compress the transducer 58 as the connecting truss member 49 is urged downwardly. The transducer 58 includes a strain sensitive material, such as a piezoelectric crystal, which is sensitive to the compression applied by the actuator 59.

To tension the fiber 22 with the apparatus 20, the fiber 22 is positioned over the hook 24 so that the ends of the fiber 22 hang on opposite sides of the hook 24. These free ends are drawn between open claims 28, 30 by suction means 72, described below. The ends of the fiber 22 are then clamped between the jaws 28, 30 of the clamping means 26 when they move to the closed position. At this starting point, the gauge, the distance between the hook 24 and the clamp means 26, is about one eighth inch (⅛"). The stepping motor 42 is subsequently actuated to rotate the shaft 46 and platform 51 is raised in the direction of the arrow A (FIG. 1). As the platform 51 is raised, the fiber 22 resists upward movement of the hook 24 so that the fiber 22 is exposed to tension forces and so that the actuator 59 is urged downward, in opposite direction to arrow A. The transducer 58 is consequently compressed so that a voltage measurement taken across the transducer 58 corresponds to the magnitude of compression to which the transducer 56 is exposed. The transducer 58 is appropriately connected to a an electronic interface 62 so that the voltage measurement taken across the transducer 58 at a predetermined instant of time corresponds proportionally to the magnitude of compression force on the transducer 58, and thus to the magnitude of the tension force applied to the fiber 22. For recording the voltage measurements taken across the transducer 58 as a function of time and for later analysis and display of such measurements, the electronic interface 62 is appropriately connected to the computer 48, which normally includes display means 68 and storage means 69.

For purposes of monitoring the elongation of the fiber 22 during a testing operation, the computer 48 which is responsible for the actuation of the motor 42 monitors the lengthwise displacement of the platform 58 with respect to time during a testing operation. This monitoring is preferably accomplished by monitoring and controlling the incremental steps of stepping motor 42, but other conventional length measuring techniques could be employed. By monitoring and controlling the motor 42, the computer 48 is able to monitor the corresponding elongation of the fiber 22 with respect to time. As is apparent herein, tensile force data collected on an individual fiber by way of the electronic interface 62 and displacement data of the platform 58 can be plotted to form two-coordinate graphical representations similar to those shown in FIGS. 7-9. It is preferred to monitor and record fiber tension forces as a function of time and fiber elongation lengths as a function of time. By causing the elongation of the fiber to be constant (linear) with respect to time, fiber elongation and time are linearly related and time can easily be converted to elongation by applying an appropriate linear function. The object is to produce a table or array of values in computer 48 containing a tension force value for each of a plurality of elongation values. Graphically, this table of values may be represented by a plot of tension force on one axis and elongation length on another axis.

With reference again to FIG. 1, the apparatus 20 also includes vacuum means 70 for drawing the ends of the fiber 22 between the jaws 28, 30 of the clamping means 26 when in the open position when preparing the apparatus 20 for testing. More specifically, as the fiber 22 is manually draped across the hook 24 and the jaws 28, 30 are spaced apart, the opposite ends of the fiber 22 are drawn between the open jaws 28, 30 by the vacuum means 70. To this end, the vacuum means 70 includes a conduit 72 appropriately connected to a vacuum source and directed generally toward the hook 24 so as to draw air between the jaws 28, 30 when they are open. With the use of the vacuum means 70, a fiber sample can be properly placed upon the hook 24 rapidly and with relative ease. Thus, the vacuum means 70 reduces the time which would otherwise be required to prepare the apparatus 20 for testing and is advantageous in this respect.

With reference again to FIG. 1, the testing apparatus 20 may be calibrated by hanging a variety of known weights on the hook 24 and recording within the computer 48 the corresponding voltages produced across the transducer 58. With information regarding the weights and the corresponding voltages measured across the transducer 58, the computer 48 can calculate during a tensioning test the amount of tension exerted upon a fiber as a function of the measured transducer voltage.

It is preferred that the environment of the area within which a fiber test is performed be precisely controlled in order to provide consistent test results. To this end a microenvironment 73 is formed around the fiber during testing. The atmosphere within the microenvironment is controlled by a test zone control system 75 that pumps a desired atmosphere, such as humid air, into the microenvironment and withdraws atmosphere from the microenvironment 73. The control system 75 monitors the atmosphere using sensors (not shown) that are placed either inside the microenvironment 73 or that are disposed to monitor the withdrawn atmosphere. The microenvironment 73 is formed preferably of transparent material such as plexiglass or vinyl and provides an opening for access to the fiber 22. The control system 75 continuously floods the microenvironment with the desired atmosphere so that leakage, even massive leakage, is permitted. In the field of processing fibers, systems have been developed to control the environment in which fibers are processed and one such system is shown in U.S. Pat. No. 4,631,781, entitled Condition Gas Flow Methods for Processing and Cleaning Fiber, Including Aeromechanical and Electrodynamic Release and Separation. An aspect of the present invention is to provide a similar environmental control in a test zone or microenvironment of a fiber testing apparatus such as shown in FIG. 1.

Figure 1C:
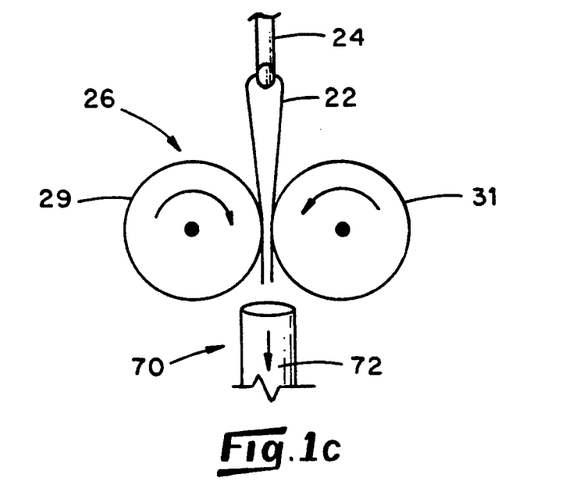
FIG. 1c is a detail view of the hook of FIG. 1a shown with a clamp in the form of rotating opposed rollers.

While the above embodiment has been described in terms of a moving hook 24 and stationary clamp means 26, it will be understood that relative movement between the two is the essential requirement, but either or both could be moving. FIG. 1c shows an alternate embodiment in which the hook 24 is stationary (at least while the fiber 22 is being broken) while the clamp means 27 moves in a rotational motion. The clamp means 27 includes two rollers 29 and 31 that are opposed, in contact, and rotate in opposite directions. A fiber 22 is positioned over the hook 24 and both are (or may be) moved into position over the rollers 29 and 31. Vacuum means 70 provided by conduit 72 draws the fiber 22 generally towards the rotating rollers 29 and 31 and, as the rollers rotate, they grip and pull the fiber 22 downwardly, elongate the fiber, place a tension on the fiber, and eventually break it. As before, elongation of the fiber corresponds to time because the rollers 29 and 31 move with constant rotational velocity. In this use the clamp means 26 provides translation of the fiber by rotational movement, but a linear movement of a clamp means could likewise provide the linear pull or translation of the fiber 22.

Figure 1D:
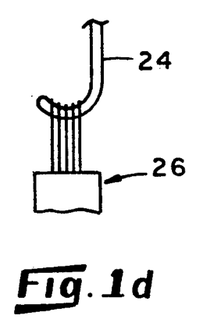
FIGS. 1d and 1e show detailed views of the hook and clamp of FIG. 1 with a parallel fiber bundle shown in FIG. 1d and a twisted bundle shown in FIG. 1e.
Figure 1E:
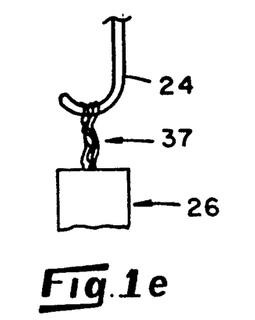

Although the embodiment of FIG. 1a is intended primarily for single fiber testing, it could be used to test multiple fibers. For example, FIG. 1d shows multiple parallel fibers 33 mounted over the hook 24 and clamped in clamp means 26 in position for break testing, and FIG. 1e shows a twisted bundle of fibers 37 similarly mounted.

Figure 3:
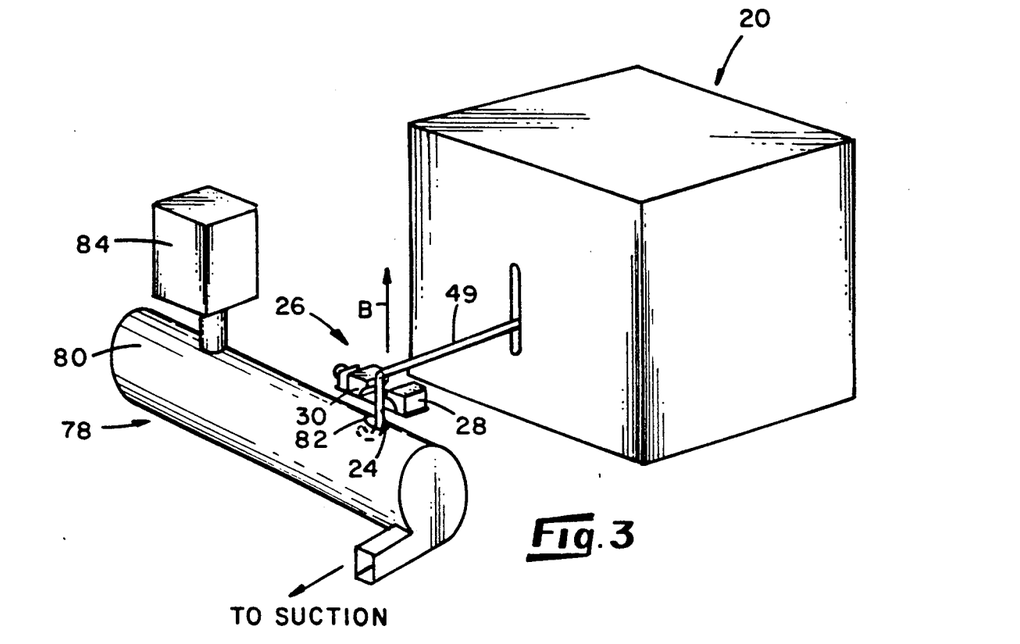
FIG. 3 is a perspective view of the FIG. 1 apparatus when used in conjunction with an automatic fiber delivery system and illustrating the condition of the apparatus when its hook is positioned in a condition for receiving a fiber delivered from the fiber delivery system.
Figure 4:
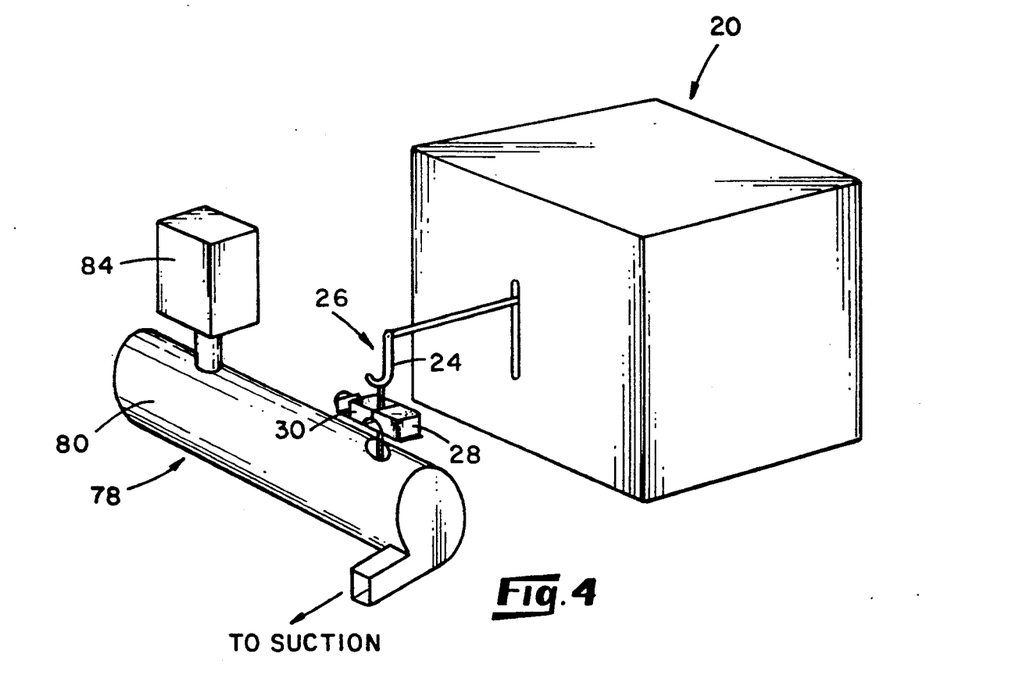
FIG. 4 is a view similar to that of FIG. 3 illustrating the condition of the apparatus when its hook is positioned in a condition for testing a fiber draped across the hook.

With reference to FIGS. 3 and 4, the FIG. 1 apparatus 20 is shown utilized in conjunction with a system, generally indicated 78 for automatically positioning a fiber (or a fiber bundle) upon the hook 24 for a testing operation. The system 78 includes an air conduit 80 having an opening 82 through which the hook 24 is lowered and raised by means of the stepping motor 42 (FIG. 1). The system 78 also includes a fiber preparation and separation device 84 for introducing a fiber into the conduit 80, and means associated with the conduit 80, such as a vacuum source and baffles (not shown), for inducing a flow of air from one conduit end to the other conduit end along a generally helical path.

When the hook 24 is in its lowered condition through the conduit opening 82 as illustrated in FIG. 3, the hook 24 is in a position for hooking a fiber moving through the conduit 80. Therefore, a fiber which is introduced into the conduit 80 and moved therethrough by the conduit airflow is caught by the hook so that the opposite ends of the fiber are draped thereacross. Once the fiber is caught, or hooked, as aforedescribed, the hook 24 is raised in the direction of the arrow B (FIG. 3) to the FIG. 4 raised condition so that the ends of the fiber are positioned between the open jaws 28, 30 of the clamping means 26. At that point, the fiber ends are clamped within the clamping means 26, and a tensile test may be performed on the fiber with the apparatus 20. By utilizing the system 78 to automatically deliver single fibers or a bundle of fibers to the hook 24 for testing purposes, a series of fiber tests may be completed at a relatively fast rate.

Figure 5:
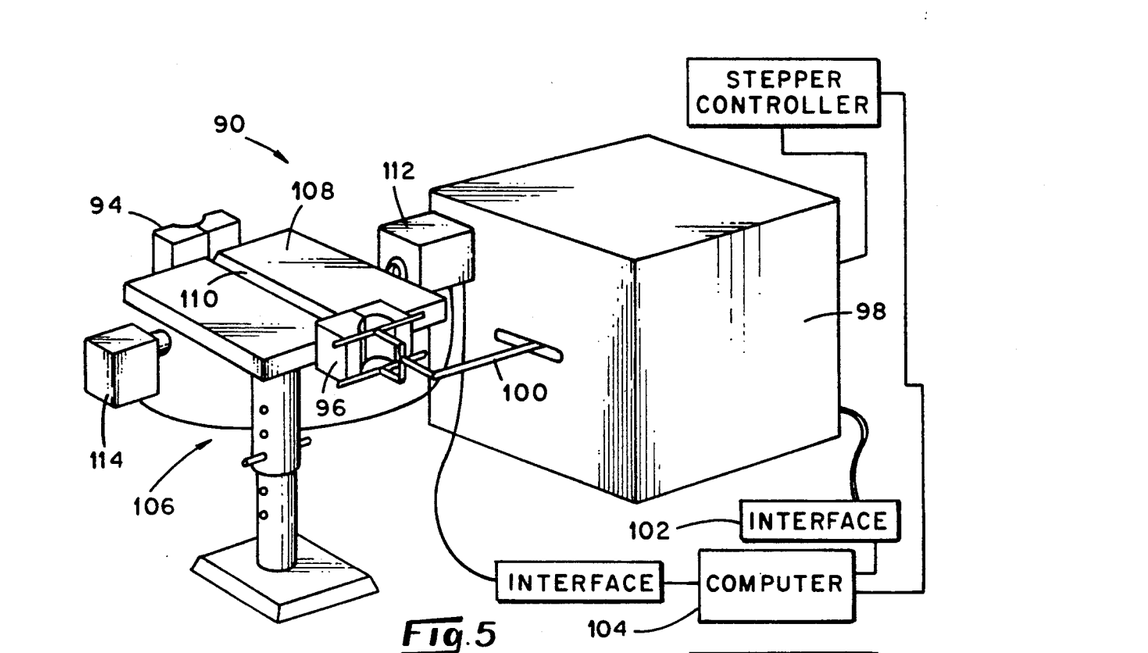
FIG. 5 is a schematic diagram of an alternative embodiment of a fiber test apparatus illustrating the relationship of various apparatus components in preparation of a testing operation.
Figure 6:
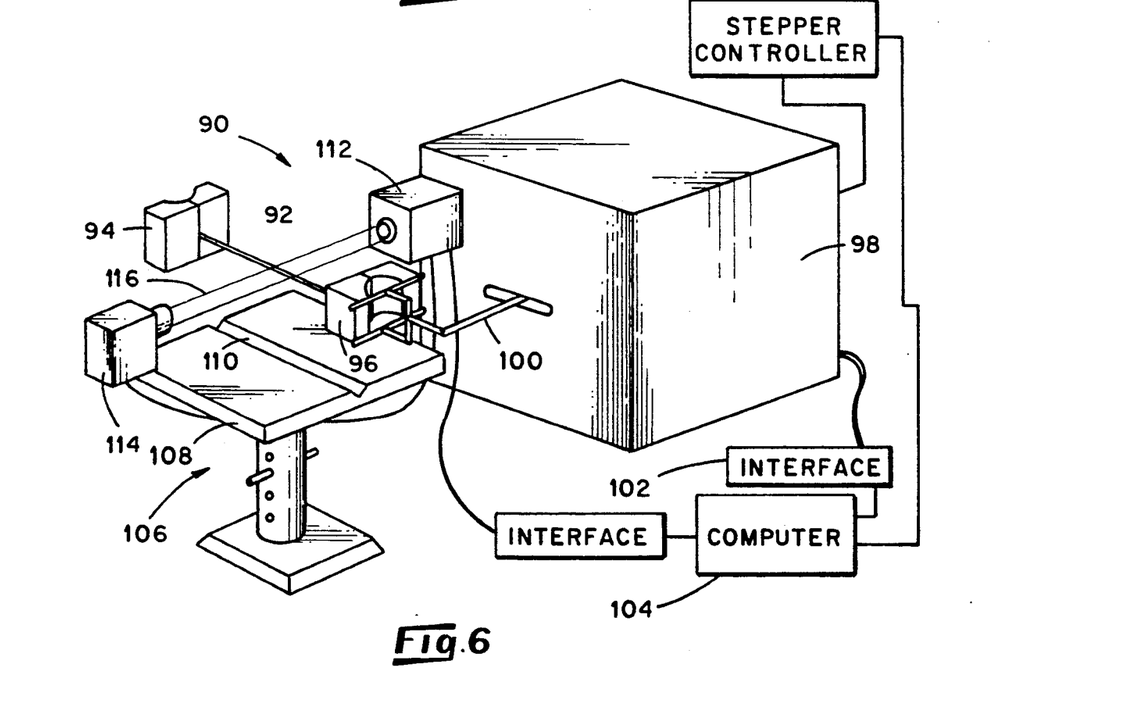
FIG. 6 is a view similar to that of FIG. 5 illustrating the relationship of various apparatus components during the course of a testing operation.

Referring to FIGS. 5 and 6, there is illustrated an alternative embodiment 90 of an apparatus for performing tensile tests on a fiber 92. The apparatus 90 includes two clamps 94, 96 arranged so that each end of the fiber 92 can be clamped within a corresponding clamp 94 or 96. One clamp 94 is mounted in a stationary condition, while the other clamp 96 is associated with a tensioning device 98 whose principles of operation are like those of the apparatus 20 of FIG. 1. It will be understood that the clamp 96 is shown diagrammatically in FIGS. 5 and 6, and in actual practice the clamp 96 will be constructed with a minimum of mass and a maximum of clamping to minimize ringing and other mass related effects. The tensioning device 98 includes a stepping motor (not shown) which is connected to the clamp 96 by means of a connecting member 100 so that by appropriate actuation of the stepping motor of the device 98, the clamp 96 can be moved away from the clamp 94 to tension the fiber 92 secured therebetween. Alternately, the clamp 94 may be moved away from clamp 96. A piezoelectric transducer (not shown) interposed between the connecting member 100 and the stepping motor of the device 98 for sensing compression as the fiber 92 is tensioned and produces a voltage corresponding to the sensed compression. The transducer of the device 98 is appropriately wired to a an electronic interface 102 and computer 104 for measuring the transducer voltage and determining the corresponding tension force. The tensioning device 98, in conjunction with computer 104 and voltmeter 102, monitors and measures tension force and elongation of the fiber in substantially the same manner as the embodiment of FIG. 1.

To facilitate the precise positioning of the fiber 92 between the clamps 94, 96 there is provided a table mechanism 106 having a platform 108 capable of movement between a raised position, as shown in FIG. 5, and a lowered position, as shown in FIG. 6. The platform 108 defines a linear V-shaped, groove 110 in its upper surface so that when positioned in the FIG. 5 raised position, the groove 110 extends between the clamps 94 and 96. When moved to its lowered FIG. 6 position, the platform 108 is removed from the vicinity of the clamps 94 and 96 and situated in an out-of-the-way condition. Air suction holes are provided in the bottom of the V-shaped groove 110 to further facilitate loading of a fiber into the groove 110.

To position a fiber 92 between the clamps 94, 96 the fiber 92 is placed within the groove 110 of the platform 108 so that its ends overhang opposite edges of the platform. The platform 108 is then raised to the FIG. 5 raised position between the clamps 94, 96 and each end of the fiber 92 is clamped within a corresponding clamp 94 or 96. During the period of time that the fiber 92 is being clamped within the clamps 94, 96 the groove 110 maintains the fiber 92 in a linear condition. Once the fiber 92 is clamped as aforedescribed, the platform 108 is lowered to the FIG. 6 position. The tensioning device 98 then moves the clamps 94, 96 relative to one another to initiate a testing operation.

The apparatus 90 further includes a source 112 of electromagnetic radiation, such as an infrared light emitting diode, supported to one side of the clamps 94, 96 and a detector 114, such as an infrared detector, supported to one side of the clamps 94, 96 opposite the light source 112. The light source 112 and detector 114 are arranged in such a relationship to the fiber 92 extending between the clamps 96, 98 so that at least a portion of a light beam 116 (FIG. 6) directed by the light source 112 toward the detector 114 interacts with the fiber, that is, is scattered or absorbed by the fiber 92. The light source 112 and detector 114 are appropriately connected to the computer 104 and to one another so that information regarding the amount of the light beam 116 scattered or absorbed by the fiber 92 is sent by the detector 114 to the computer 104. By comparing the amount of light detected by the detector 114 when the fiber is positioned in the beam 116 to the amount of light detected by the detector 114 when the fiber is not positioned in the beam 116, the computer 104 can determine characteristics relating to the cross section of the fiber 92. Such characteristics may include, for example, the diameter of the fiber cross section For purposes of comparing the amount of light detected by the detector 114 to known values, the computer 104 has been preprogrammed with cross sectional information relating to several calibration fibers with known diameters and the corresponding amounts of light which are sensed by the detector when those fibers are positioned within the light beam. Although FIG. 6 shows an embodiment in which the detector responds to extinction, other detector positions would also work. For example, one may wish to monitor forward scattered light ($\approx 45°$) or measure the amount of light backscattered ($\approx 180°$) by the fiber depending in a particular application. As used herein, the term scattered light will be used in a broad sense and is intended to include back, side and forward scattering.

The light source 112 and detector 114 thus provide means by which cross sectional characteristics of a fiber may be monitored as the fiber is being tensioned with the tensioning device 98. Therefore, multivariate data consisting of force, elongation and cross-sectional information can be gathered by the computer 104 for a single fiber in a single testing operation. It will be understood that the light source 112 and detector 114 may also be used with the apparatus 20 of FIG. 1 to determine cross sectional information as a test with the apparatus 20 is performed. This variation is shown in FIG. 1b.

Figure 7:
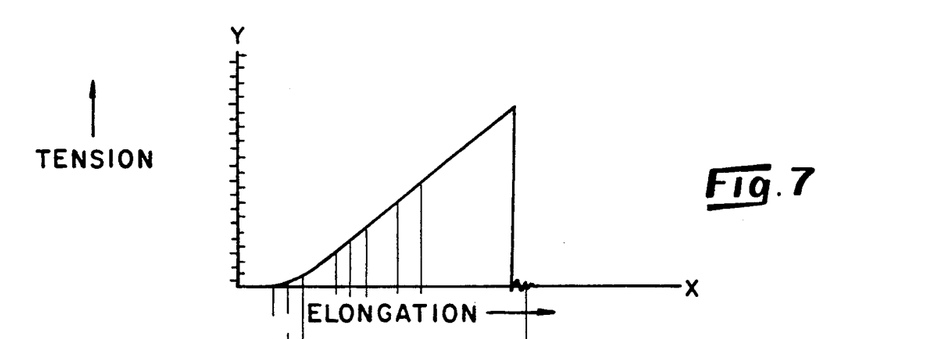
FIGS. 7-9 are graphical representations of test results carried out on individual fiber samples.
Figure 8:
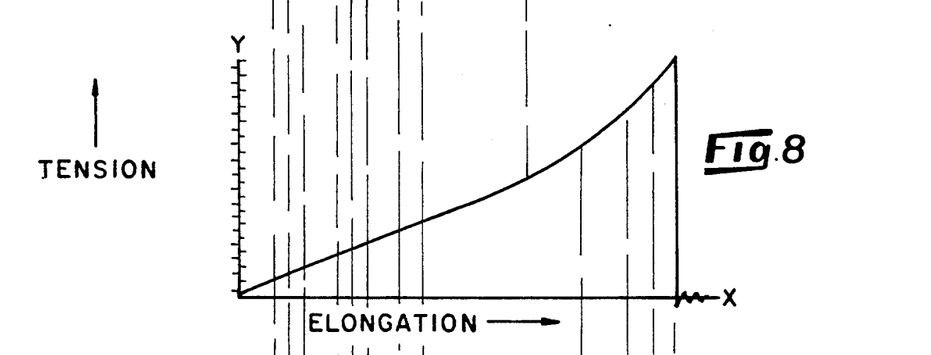
Figures 9, 10:
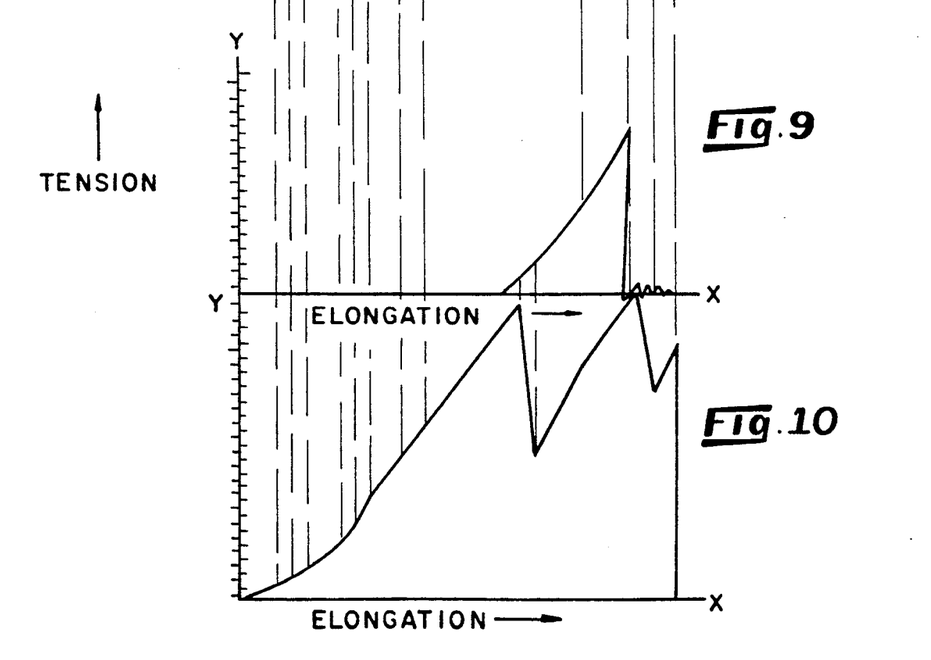
FIG. 10 is a graphical representation obtained by superimposing information borne by the graphs of FIGS. 7-9 onto a single graph.
Figure 11:
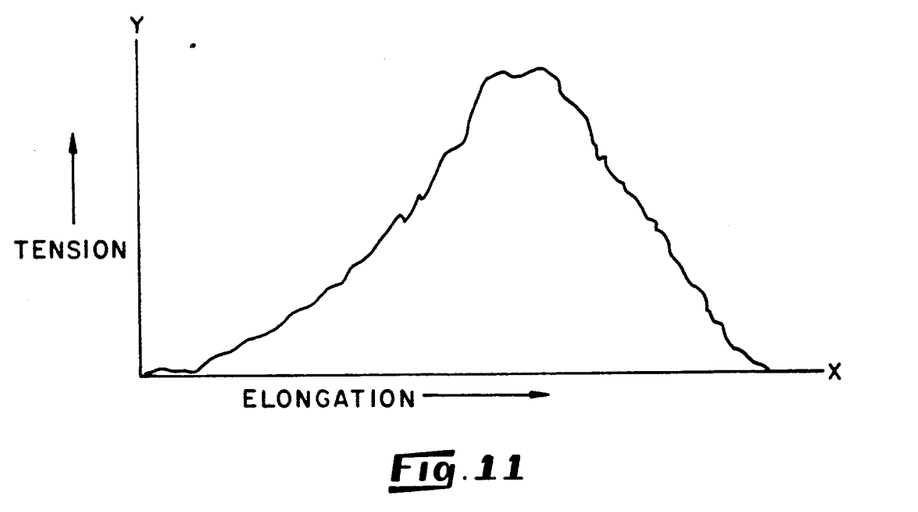
FIG. 11 is a graphical representation obtained by superimposing information borne by a large number of graphs like those of FIGS. 7-10 onto a single graph.

With reference to FIGS. 7-9, there are shown two-coordinate graphical representations of elongation and tensile data collected when subjecting three fibers to a tensile test with the apparatus 20 of FIG. 1. More specifically, FIG. 7 is a graphical representation of the test results gathered when tensioning a first fiber until it breaks; FIG. 8 is a graphical representation of the test results gathered when tensioning a second fiber until it breaks; and FIG. 9 is a graphical representation of the test results gathered when tensioning a third fiber until it breaks. In each graph of FIGS. 7-9, the magnitude of the fiber elongation is plotted along the abscissa, and the corresponding magnitude of the tensile forces is plotted along the ordinate.

In the computer 48 of FIG. 1 or 104 of FIG. 5, the force-elongation readings are stored in ordered arrays corresponding to ordered pairs (x,y) on each of FIGS. 7-9. The locus of all such ordered pairs is simply the force-elongation graph. Since equal x-values correspond to identical values of elongation, and since elongation is directly proportional to time, the same x-value corresponds to alignment in time; thus the graphs of FIGS. 7-9 can be called "time-aligned arrays".

That is, for emphasis, time-aligned force-elongation arrays can be manipulated to model the total force on the hook for a multiplicity of fibers. This will now be explained using the graphical representations of FIGS. 7-9.

In order to predict the tensile characteristics of a bundle of fibers comprised of the three fibers whose test results are graphically illustrated in FIGS. 7-9, the graphical representations of FIGS. 7-9 may be superposed on one another to form the graph of FIG. 10. To superpose the graphs of FIGS. 7-9, the tensile stress values of the graphical representations for a preselected elongation magnitude are added together to obtain one additive stress value, and the additive stress value is plotted on a secondary graph (i.e., the graph of FIG. 10) wherein a range of stress values is represented along the ordinate of the secondary graph and a range of elongation magnitudes is plotted along the abscissa of the secondary graph. The tensile stress values identified on FIGS. 7-9 for a number of other preselected elongation magnitudes are also added together and the locus of resulting additive values plotted on the secondary graph is the resulting graphical representation predicted tensile characteristics of the fiber bundle over a relatively broad range of elongation magnitudes.

The information shown in the secondary graph, FIG. 10, may be termed multiple fiber data and as explained above it correlates to some extent with fiber bundle test, but it is not duplicative of any known bundle test. While the technique of deriving the secondary graph of FIG. 10 has been described with reference to three fibers, in actual practice, many fibers (on the order of 100's) will be tested to provide accurate data as to a particular sample of fibers.

Also, it will be understood that the data shown in FIGS. 7-10 has been chosen to best illustrate the invention and it does not represent any particular fiber sample. It should be noted that the fiber of FIG. 9 elongated for a significant period of time without any tension being produced in the fiber (high crimp), but the fiber of FIG. 8 experienced a tension force immediately upon elongation (low crimp). Usually, elongation of a fiber without placing tension forces on the fiber indicates that the fiber was crimped and the initial elongation is removing crimp. These graphs indicate that the FIG. 9 fiber had a very large amount of crimp, while the FIG. 8 fiber had zero crimp. The difference in the amount of crimp helps illustrate the invention.

The above described method of obtaining multiple fiber data is not limited to tension and elongation data. For example, in an alternate embodiment, cross section data, such as area, diameter or thickness are substituted for elongation and alignment of the data is accomplished according to either time or the cross-sectional data. Also, the multiple fiber data is not limited to two dimensions. For example, one may also produce three coordinate arrays (or three dimensional graphs) using, for example, elongation, tension, and a cross sectional characteristic. For example, in a three coordinate array, tension and cross-sectional characteristics could be plotted with respect to elongation or time as was the case in the two coordinate array.

It will be understood that numerous modifications and substitutions can be had to the aforedescribed embodiments without departing from the spirit of the invention. Accordingly, the aforedescribed embodiments are intended for the purpose of illustration and not as limitation.

What is claimed is:

1. A method for producing multiple fiber data, comprising:
  a) tensioning at least one fiber from a sample composed of a plurality of fibers;
  b) increasing the tension on the fiber to elongate and eventually break the fiber;
  c) as the fiber is elongated and broken, measuring tension force on the fiber and elongation length of the fiber;
  d) recording the tension force on the fiber at a plurality of elongation lengths and thereby creating an array of tension forces and corresponding elongation lengths;
  e) repeating steps a through d for a predetermined number of fibers from the sample to produce a predetermined number of arrays; and
  f) for each elongation length in the arrays, adding the tension forces to produce a composite array containing a tension force sum for each one of the plurality of elongation lengths, said composite array constituting multiple fiber data as the strength characteristics of the fibers as a whole in a bundle.

2. The method of claim 1 further comprising the steps of:
  directing radiation toward the fiber being tested generally from one side thereof;
  detecting radiation directed toward the fiber and scattered by the fiber;
  producing a signal corresponding to the detected radiation; and
  determining a cross sectional characteristic of the fiber in response to the produced signal.

3. A method for predicting the characteristics of a bundle of fibers containing a plurality of fibers comprising:
  providing a two-coordinate graphical representation of elongation and tension characteristics of a predetermined number of fibers in the bundle wherein the magnitude of fiber elongation is plotted along one coordinate of the graphical representation and the magnitude of tension force exerted upon the fiber is plotted along the other coordinate of the graphical representation,
  adding tension force values of the graphical representations together for a preselected elongation magnitude to obtain an additive force value and plotting the additive force value on a secondary two-coordinate graph wherein one coordinate of the secondary graph denotes elongation magnitudes and the other coordinate of the secondary graph denotes a range of additive force values, and
  repeating the addition of tension force values together for a number of other preselected elongation magnitudes identified on the graphical representations and plotting the resultant additive values on the secondary graph to obtain a secondary graphical representation of predicted tension characteristics of the fiber bundle over a relatively broad range of elongation magnitudes.

4. A method for producing multiple fiber data as to fibers taken from a sample composed of fibers;
  performing a first test to determine first and second characteristics of at least one fiber taken from the sample;
  producing and storing a first representation of the first and second characteristics of said first test;
  performing at least a second test to determine first and second characteristics of at least one additional fiber taken from the sample;
  producing and storing a second representation of the first and second characteristics of the second test; and
  combining the first and second representations to produce a composite representation of the first and second characteristics for all fibers that were tested, said composite representation having first and second characteristics and constituting multiple fiber data.

5. The method of claim 4 wherein said combining step comprises:
  aligning the first and second representations according to the first characteristic so that, for identical first characteristics in the first and second representations, the second characteristics will be aligned; and
  adding the aligned second characteristics of the first and second representations to form the second characteristics in the composite representation.

6. The method of claim 5 wherein said first characteristic is elongation of the fiber and said second characteristic is a tension on the fiber.

7. The method of claim 5 wherein said first characteristic is tension on the fiber and said second characteristic is a cross-sectional characteristic of the fiber.

8. The method of claim 5 further comprising monitoring and determining a third characteristic of the fibers during each of said tests and combining the first, second and third characteristics of the representations to produce the composite representation.

* * * * *